United States Patent
Starchevich

(10) Patent No.: US 6,311,933 B1
(45) Date of Patent: *Nov. 6, 2001

(54) COMBINATION HOLDING AND STABILIZING DEVICE WITH REINFORCEMENT

(76) Inventor: Jovanka Starchevich, 138 Sullivan St., New York, NY (US) 10012

( * ) Notice: Subject to any disclaimer, the term of this patent is extended or adjusted under 35 U.S.C. 154(b) by 0 days.

This patent is subject to a terminal disclaimer.

(21) Appl. No.: 09/483,848

(22) Filed: Jan. 17, 2000

Related U.S. Application Data

(63) Continuation-in-part of application No. 09/197,048, filed on Nov. 20, 1998, now Pat. No. 6,015,119.
(60) Provisional application No. 60/105,860, filed on Oct. 27, 1998.

(51) Int. Cl.$^7$ ........................................................ F16L 3/08
(52) U.S. Cl. ........................ 248/65; 128/DIG. 6; 604/180
(58) Field of Search ........................ 248/65, 74.3, 205.2, 248/903; 604/180; 128/DIG. 6

(56) References Cited

U.S. PATENT DOCUMENTS

| | | | |
|---|---|---|---|
| 3,630,195 | * 12/1971 | Santomieri | 128/DIG. 6 X |
| 3,834,380 | * 9/1974 | Boyd | 128/DIG. 6 X |
| 4,706,914 | * 11/1987 | Ground | 248/74.3 |
| 5,389,082 | * 2/1995 | Baugues et al. | 604/180 X |
| 5,390,883 | * 2/1995 | Songhurst | 248/74.3 |
| 5,709,665 | * 1/1998 | Vergano et al. | 604/180 X |
| 5,810,781 | * 9/1998 | Bierman | 604/180 X |
| 5,827,230 | * 10/1998 | Bierman | 604/180 X |

* cited by examiner

Primary Examiner—Ramon O. Ramirez
(74) Attorney, Agent, or Firm—Howard C. Miskin; Gloria Tsui-Yip

(57) ABSTRACT

A combination holding and stabilizing device with reinforcement for cylindrical objects comprises a combination of two components, a securing unit and an anchoring unit. The securing unit has an elongated longitudinal body having a top surface with adhesive and first and second lateral portions extending from a fold line. The second lateral portion foldably overlaps the first lateral portion for holding and stabilizing a cylindrical object therebetween. At both ends of the body, the top surface of the first and second portions have separable holding elements to releasably secure the first and second portions together to allow quick and easy adjustment of the cylindrical object. The securing unit has at least one reinforcement strip embedded in the body for improving the holding and stabilizing power. The plastic strip is malleable and conforms to the shape of the cylindrical object to be held in the securing unit. The plastic strip may have various shapes and form different patterns for enhanced holding and stabilizing power. The securing unit with reinforcement strip may be used alone to maintain the shape and form of a cylindrical object or in combination with the anchoring unit to hold and stabilize the cylindrical object.

19 Claims, 12 Drawing Sheets

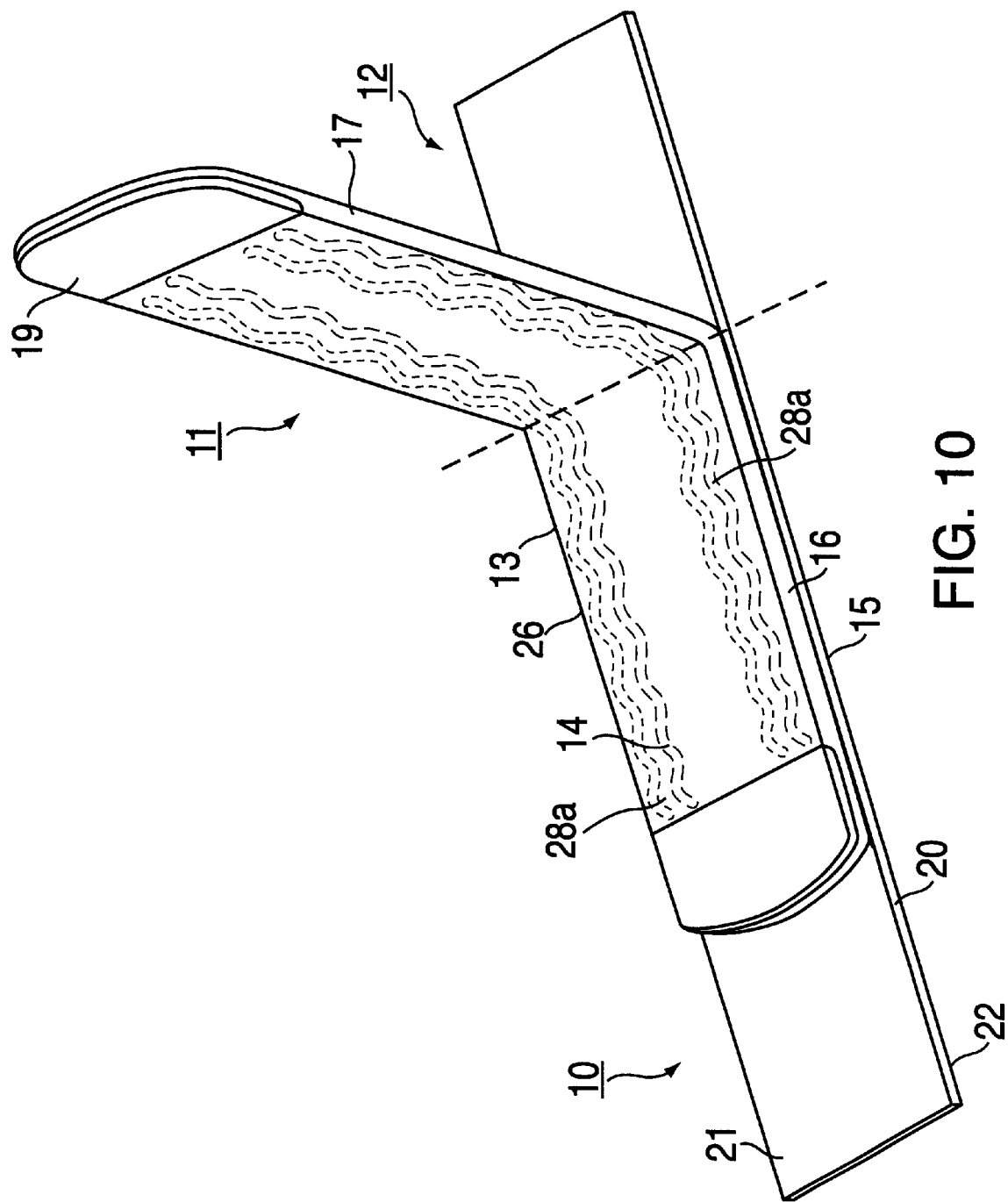

COMBINATION HOLDING AND STABILIZING DEVICE WITH REINFORCEMENT

This is a continuation in part of application Ser. No. 09/197,048, filed Nov. 20, 1998, now U.S. Pat. No. 6,015,119, which claims benefit of Provisional No. 60/105,860 filed Oct. 27, 1998.

FIELD OF THE INVENTION

The invention relates to a device for securely retaining and stabilizing tubular, cylindrical or similar objects and maintaining their forms. In particular, a combination holder and stabilizer with reinforcement for securing and maintaining medical tubes, rods and/or catheters applied to a patient.

BACKGROUND OF THE INVENTION

In the medical field, cylinders, tubes and catheters are routinely used to interface different parts of a patient's body, such as for infusion and drainage therapies. For example, intravenous (I.V.) treatment, Foley catheters, nasal gastric treatment, wound suction or drainage, evacuators tubing, gravity drains, urinary tubes, etc. Infusion and drainage therapies are often cumbersome and uncomfortable to the patient as it requires the connection and support of tubes and/or catheters to the patient. Discomfort to a patient increases if the tube and/or catheter is not securely attached to the patient in an accurate position. Furthermore, a twisted or tangled tube and/or catheter may detrimentally affect the flow of the treatment or drainage. In many instances, the positioning, stability and secured retainment of the tubes and/or catheters is crucial to the outcome of the treatment, and certainly to the comfort of the patient on which it is used.

A twisted or insecurely retained tube and/or catheter can lead to many complications and cause discomfort to the patient, such as decreasing the flow of treatment or drainage or accidentally withdrawing it from the patient's body, which disrupts the treatment. Even in cases where the insecurely retained tube and/or catheter is not completely removed from the body, needless interference with the positioning and shape of the tube and/or catheter can cause problems to the patient. For example, a twisted tube may cut off the natural flow of the treatment or drainage. An unexpected, inadvertent movement of an I.V. tube can cause the needle to damage the wall of the vein or blood vessel. For nasal gastric treatment, constant accurate positioning of the tube in the nostril and through the nasal passage is critical. An improperly positioned tube can cause the tube to either adhere to the stomach walls and cause the stomach lining to bleed or cause erosion through the nasal septum and, in extreme cases create a hole in the nasal septum.

The traditional method of securing tubes and/or catheters to a patient and maintaining their forms is the use of adhesive tapes such as surgical tape or bandage. Adhesive tapes cannot securely retain tubes and/or catheters for accurate positioning due to the thinness and pliability of the tapes. The tube and/or catheters may be accidentally twisted or removed from the patient from the patient's own movement. Secure retainment is compromised if the adhesive power of non-surgical grade tape is traded off for breathability of the skin of surgical tape for minimal irritation. Stability of the tube and/or catheter is further compromised by having the tube and/or catheter rests directly against the flexible, compressible and movable skin of a patient.

During the course of an infusion or drainage treatment, which can last for several weeks to several months, it is often necessary to adjust the positioning of the tube and/or catheter during use. The traditional use of adhesive tape to secure a tube and/or catheter does not provide an easy method of adjustment of the tube and/or catheter. To adjust these normally requires the removal and replacement of the adhesive tape after repositioning the tube and/or catheter because the adhesive power of the tape decreases substantially from the oily excretions from the patient's skin. Over a period of time, such removal and replacement of the tape causes discomfort to the patient, such as sensitive skin, irritation and pain.

Therefore, there is a need for a device that comfortably, quickly and securely retains and stabilizes tubes and/or catheters applied to a patient and maintains their forms yet facilitates easy repositioning and readjustment of the tubes and/or catheters, with little discomfort to the patient.

SUMMARY OF THE INVENTION

The invention provides a combination holding and stabilizing device that quickly and securely positions and retains tubes and/or cylinders such as catheters and maintains their form to facilitate shaping and repositioning of the tube and/or catheter with a minimum of discomfort to the patient.

The combination holding and stabilizing device of the present invention preferably comprises a combination of two components, a securing unit and an anchoring unit. The securing unit is for holding and stabilizing a cylinder, tube and/or catheter at a constant position relative to the device of the present invention. The anchoring unit is for holding and stabilizing the securing unit at a constant position relative to a fixed location, such as a patient's body. The securing and anchoring units work cooperatively to achieve the optimal retainment, flexibility in choice of placement, and security of tubes and/or catheters to a patient.

The securing unit of the present invention has preferably a generally elongated body such as a rectangular shaped longitudinal body made of a layer of thin flexible foam having a first top surface and a second bottom surface. The body has first and second lateral portions, preferably equal in size, extending from a fold line whereby the second lateral portion foldably overlays the first lateral portion. The top surface of the body has a resealable adhesive for securing a tube and/or catheter sandwiched between the first portion and the second overlay portion along the axis of the folding line for optimal stability. Advantageously, at both ends of the elongated body, the top surface of the first and second portions have separable holding elements such as corresponding hooks and loops of a VELCRO™ interlocking mechanism to both releasably secure the first and second portions together and to facilitate separation of the second overlay portion from the first portion for quick and easy adjustment of the tube and/or catheter.

Illustratively, the anchoring unit of the present invention has a rectangular shaped longitudinal body, similar to the securing unit, having a first top surface and a second bottom surface. The bottom surface has adhesive for attaching to a fixed location. The anchoring unit has a length proportionally longer than the first portion of the securing unit. The bottom surface of the first portion of the securing unit is attached to the top surface of the anchoring unit with the anchoring unit extending beyond at least the axis of the fold line of the securing unit to provide maximum anchoring and stability to the tubes and catheters secured in the securing unit. It is preferable that the anchoring unit is a medical-grade adhesive tape, which is generally known to one skilled in the art, that is suitable for application to a patient's skin.

In an alternative embodiment of the present invention, the foam body of the securing unit has at least one generally rectangular thin plastic strip embedded longitudinally across the body. The plastic strip is malleable and pliable to the extent that when it is pressed against the tube and/or catheter in the securing unit, it molds and conforms to the shape of the tube and/or catheter to increase and reinforce the holding and stabilizing power of the securing unit. Such plastics having this ability are well known in the art. Another advantage of using plastic strips is the ability to generally decrease the thickness of the foam body without losing the holding and stabilizing power of a thicker and firmer foam.

The thin plastic strip embedded in the body may alternatively have a wave-like structure. One or more of the wave-like strip may be embedded longitudinally across the body, either horizontally or vertically in relation to the top and bottom surfaces of the body of the securing unit. When a wave-like strip is embedded horizontally, it improves the holding and stabilizing power of the securing unit yet provides the flexibility to mold and conform the securing unit around a tube and/or catheter. A horizontally embedded double-wave strip further reinforces the securing unit over a single-wave or rectangular strip. When a wave-like strip is embedded vertically, the indentation of each wave may correspond to the diameter of a tube and/or catheter to improve the holding and stabilizing power of the securing unit without requiring much force to mold and conform.

Alternatively, a plurality of thin strips may be embedded spaced-apart, in parallel and at an angle relative to the fold line of the securing unit such that when the second lateral portion of the body foldably overlays the first lateral portion, the plurality of thin strips produce a cross-hatch pattern. Similarly, a plurality of thin strips may be embedded in a cross-hatch or mesh pattern to further reinforce the holding and stabilizing power of the securing unit.

The securing unit with reinforced strips may be used alone, without the anchoring unit, to maintain the shape and form of a tube and/or catheter. As such, the securing unit serves the dual purpose of maintaining the form of a tube and/or catheter and holding and stabilizing the tube and/or catheter when used in conjunction with the anchoring unit.

BRIEF DESCRIPTION OF THE DRAWINGS

These and other features of the invention are delineated in detail in the following description. In the drawings:

FIG. 10 is a perspective view of the present invention with a double wave strip embedded horizontally.

It will be appreciated that, for purposes of illustration, these figures are not necessarily drawn to scale.

DETAILED DESCRIPTION OF THE PREFERRED EMBODIMENTS

Figure 1:
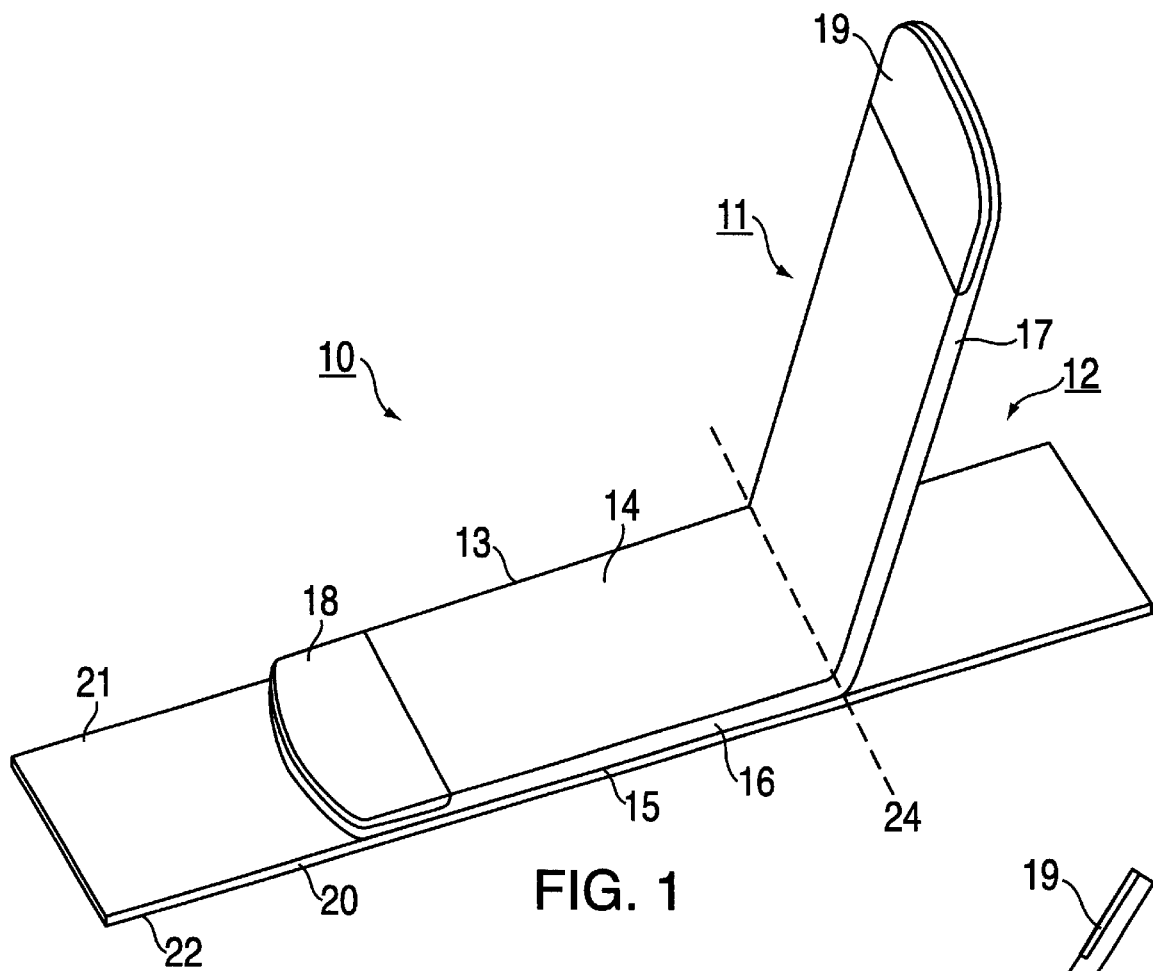
FIG. 1 is a perspective view of the present invention.

With reference to the drawings, wherein the same reference number indicates the same element throughout, there is shown in FIG. 1 a perspective view of the present invention. The present invention, a combination holding and stabilizing device 10 comprises a securing unit 11 atop an anchoring unit 12.

Figure 2:
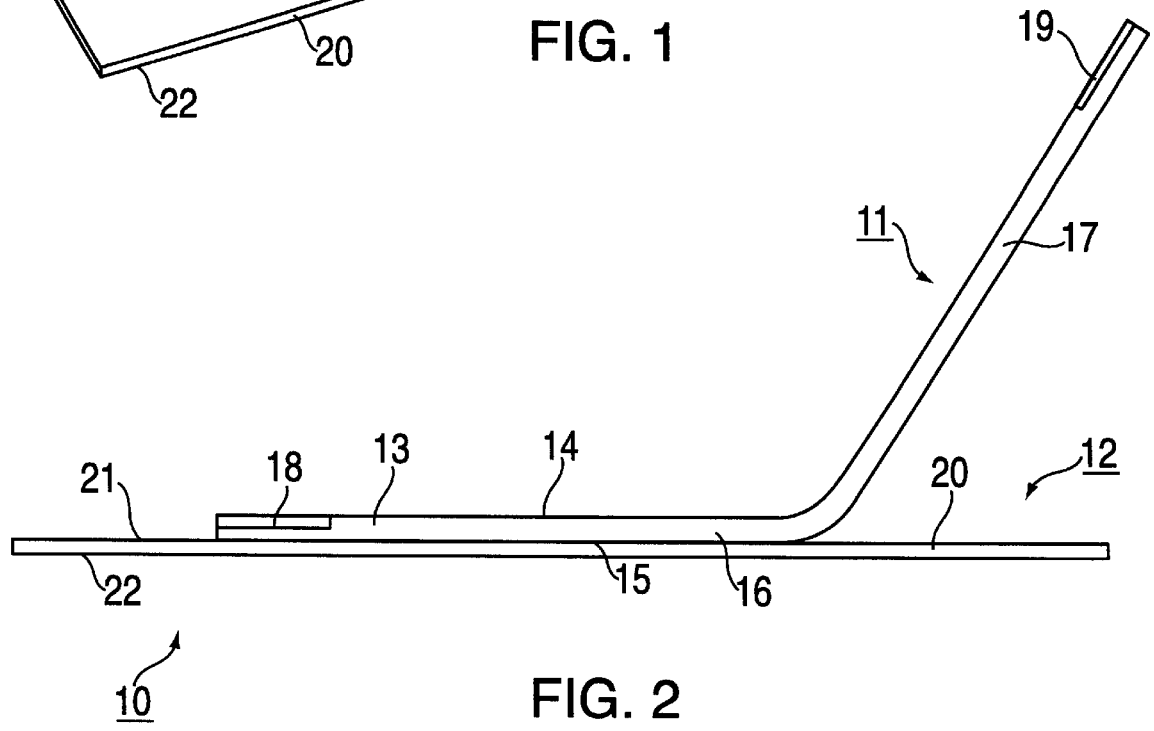
FIG. 2 is a front elevational view of FIG. 1.
Figure 5:
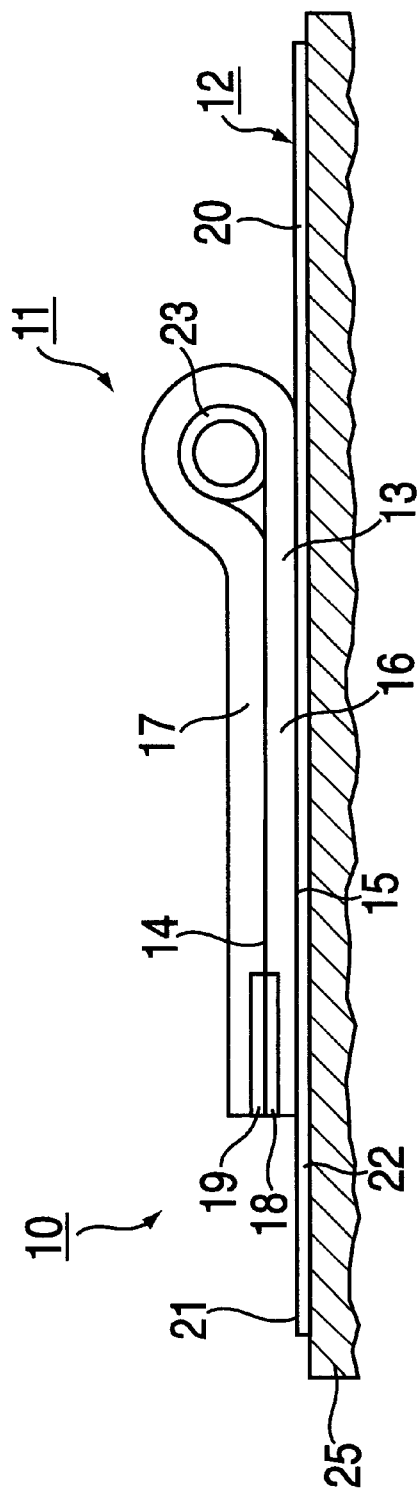
FIG. 5 is a front elevational view illustrating the retainment and stability of a tube and/or catheter with the present invention applied to a patient.

As shown in FIGS. 1 and 2, securing unit 11 has a generally rectangular shaped longitudinal body 13 having a top surface 14 and a bottom surface 15. Body 13 has first and second lateral portions 16 and 17, preferably of equal size, whereby the second portion 17 foldably overlays and overlaps the first portion 16. Top surface 14 of body 13 has resealable adhesive for securing a tube and/or catheter placed sandwiched between the first and second portions 16 and 17, as shown in FIG. 5. At each opposite end 18 and 19 of body 13, on the top surface 14, are corresponding hooks and loops, respectively, of a VELCRO™ interlocking mechanism.

Body 13 is preferably made of a layer of thin foam to provide flexibility yet firmness to secure a tube and/or catheter, but other materials know to one skilled in the art, such as pile fabric, may be substituted. Body 13 also serves to absorb moisture and oil excretion from a patient's body. The length of body 13 may vary proportionally to the diameter of the tubes and/or catheters to be secured for maximum secure holding and stability.

The anchoring unit 12 has a generally rectangular shaped longitudinal body 20, similar to body 13 of securing unit 11, having a top surface 21 and a bottom surface 22. The bottom surface 15 of the first portion 16 of securing unit 11 is attached to the top surface 21 of anchoring unit 12 by means known to one skilled in the art, such as gluing, sewing, stapling, VELCRO™ interlocking mechanism, etc. Body 20 of anchoring unit 12 is longer than the first portion 16 of securing unit 11.

Body 20 of anchoring unit 12 is preferably a medical-grade adhesive tape that is suitable for application on a patient skin, such as hydrocolloid adhesive tape that resists breakdown from skin moisture and adhere to skin well but not hair, which is available from, for example, 3M™. The length of body 20 may vary proportionally to the length of the first portion 16 of securing unit 11 for maximum secure holding and stability of the securing unit 11 and the tube and/or catheter attached to securing unit 11.

Figure 3:
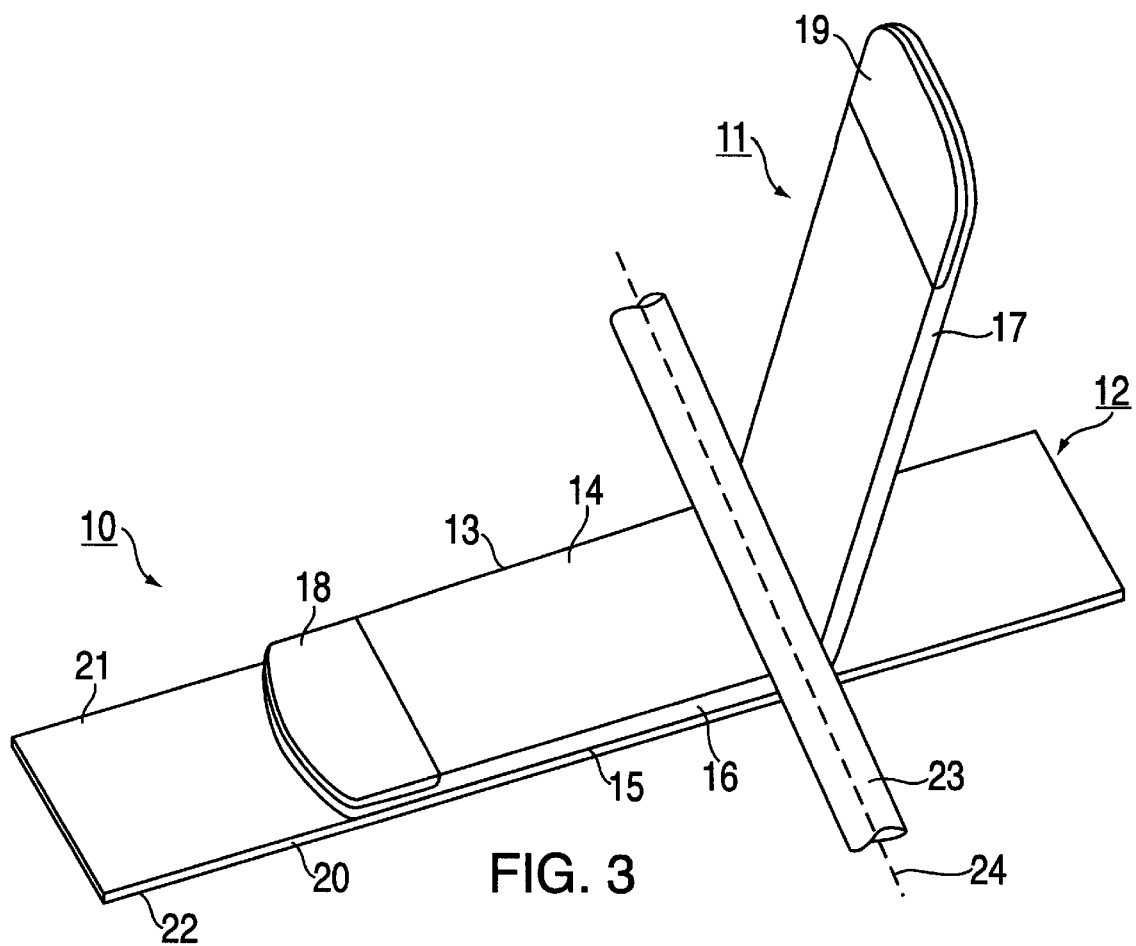
FIG. 3 is a perspective view illustrating the positioning of a tube and/or catheter for maximum retainment and stability.
Figure 4:
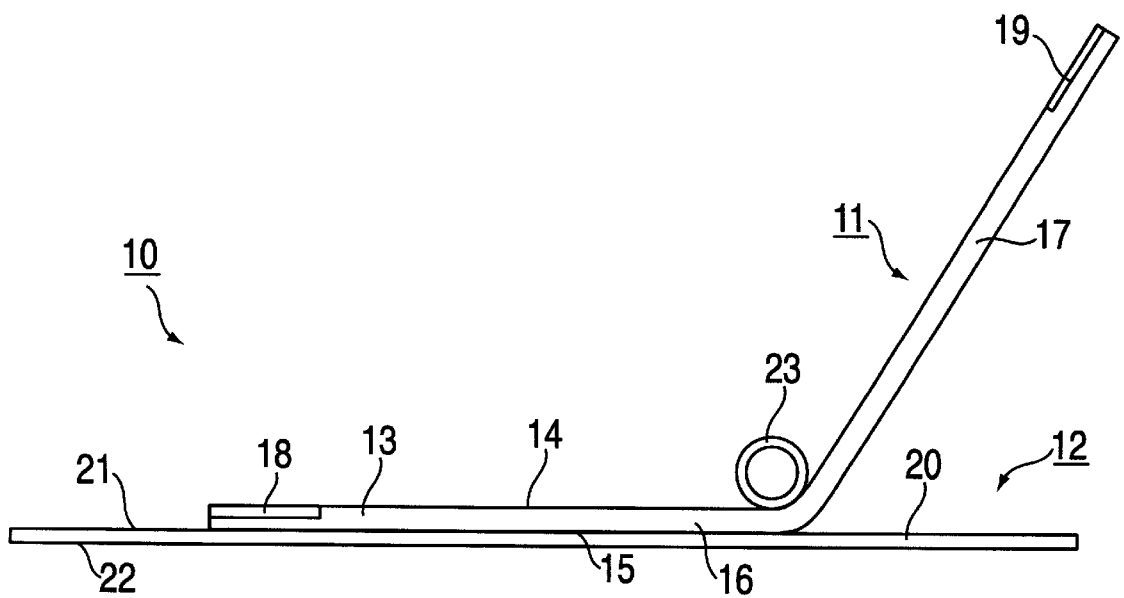
FIG. 4 is a front elevational view of FIG. 3.

The application of the combination holding and stabilizing device 10 is demonstrated with FIGS. 3, 4 and 5. FIGS. 3 and 4 illustrate the positioning of a tube and/or catheter 23 perpendicular to longitudinal body 13 of securing unit 11 along the axis of the fold line 24 where second portion 17 foldably overlays first portion 16 about fold line 24.

As shown in FIG. 5, second portion 17 is folded to overlay first portion 16 of securing unit 11. The resealable adhesive on top surface 14 of securing unit 11 causes first portion 16 to adhere to second portion 17 and sandwiched tube 23 therebetween. Similarly, the hooks and loops at ends 18 and 19, respectively, of securing unit 11 interact to secure the first portion 16 to second portion 17. With tube 23 in alignment with the axis of the fold line 24 and top surface 14 of securing unit 11 adhering to the surface of tube 23, tube 23 is restricted from movement in all directions. The stability of tube 23 is enhanced with the support of foam body 13 of securing unit 11 along the axis of the fold line 24 across the width of body 13.

The anchoring unit 12 in FIG. 5 is applied to a patient's body 25. The adhesive tape of body 20 of anchoring unit 12 is applied to the surface of the patient's skin and can conform to different contour of the body, such as finger, arm, nose and thigh, to be securely attached thereto. As can be seen in FIG. 5, to provide maximum retainment and stability to tube 23 in securing unit 11, anchoring unit 12 extends beyond, at least, the first portion 16 where the second portion 17 folds over the first portion 16.

The removal and adjustment of tube 23 can be easily achieved without disturbing the patient to which the combination holding and stabilizing device 10 is attached. The hooks and loops at ends 18 and 19, respectively, of securing unit 11 can be easily separated to expose top surface 14 of both the first portion 16 and the second portion 17 and tube 23, whereby tube 23 may be repositioned before again folding second portion 17 over first portion 16 to securely retain tube 23.

Figure 7:
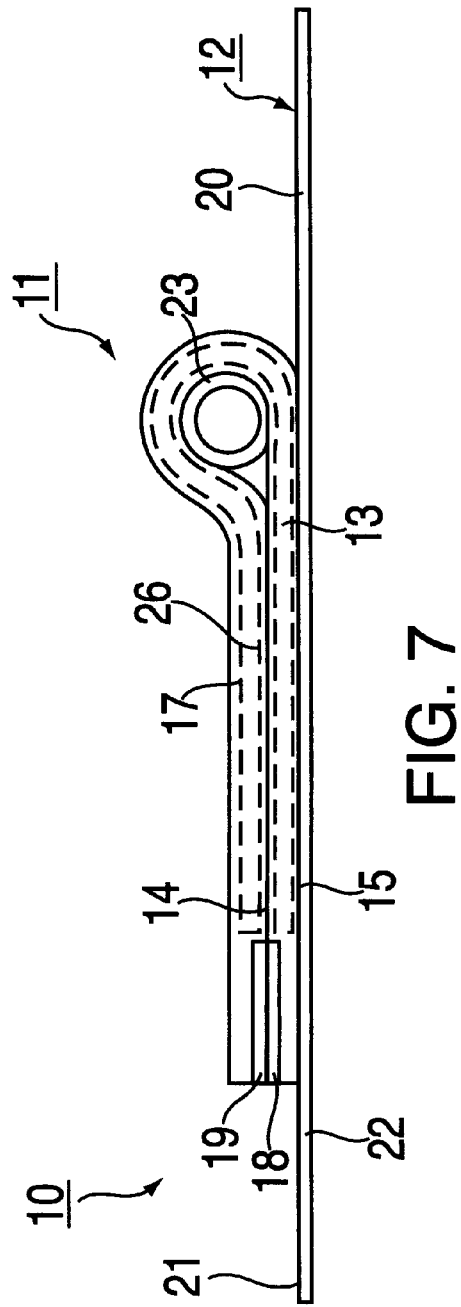
FIG. 7 is a front elevational view illustrating the retainment and stability of a tube and/or catheter in a second embodiment of the present invention.
Figure 6:
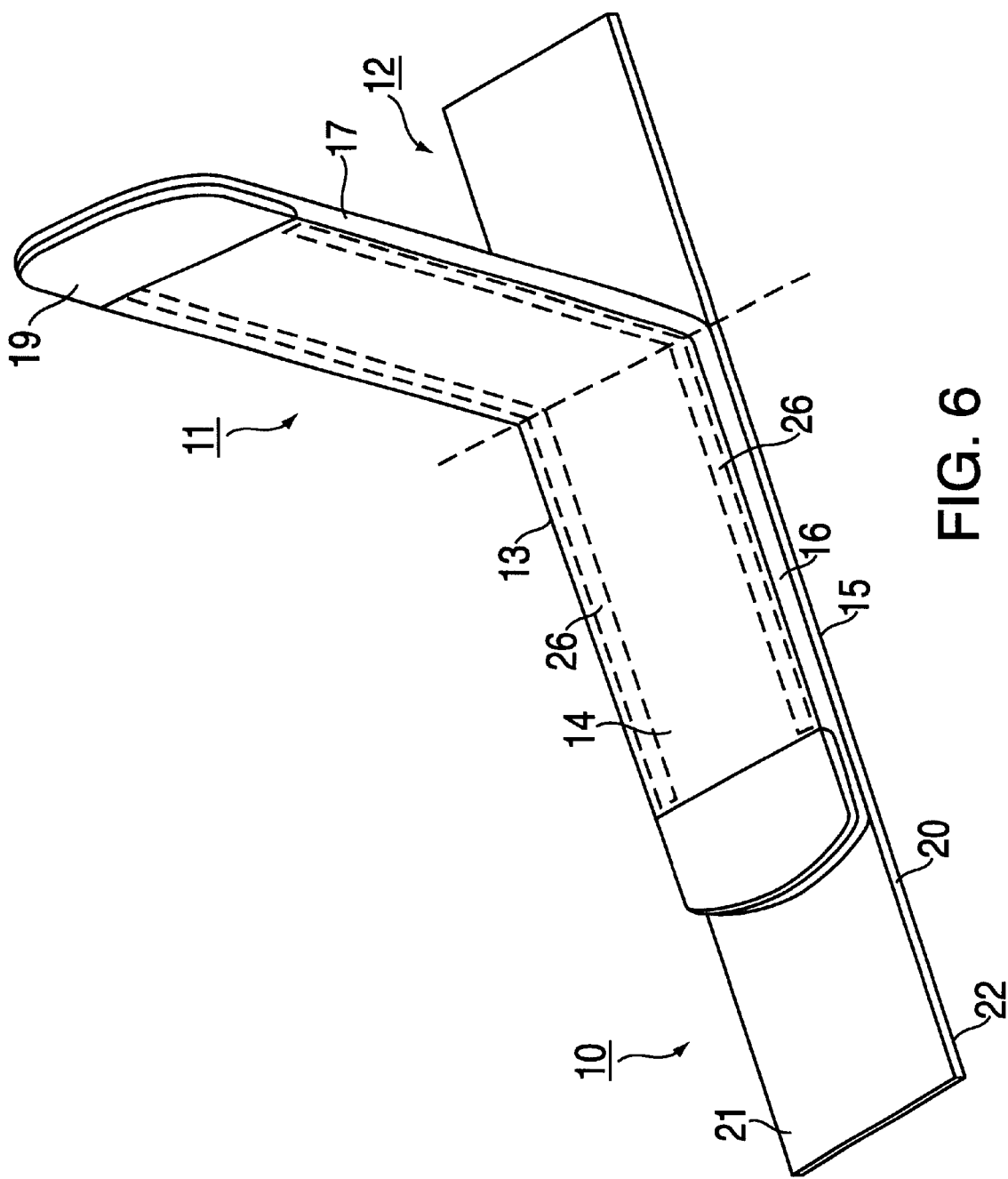
FIG. 6 is a perspective view of a second embodiment of the present invention.

An alternate embodiment of the present invention is shown in FIGS. 6 and 7, wherein two generally rectangular plastic strips 26 are embedded longitudinally along body 13 of securing unit 11 to reinforce the holding and stabilizing power of the securing unit 11. The plastic strips 26 are malleable, pliable and capable of conforming to the contour of tube 23 for added secure retainment and stability, as shown in FIG. 7. After positioning tube 23 between first and second portions 16 and 17 of securing unit 11, the plastic strips 26 are molded to act as a skeleton to hold tube 23 in a stable position. The addition of plastic strips 26 allow, generally, the decrease in thickness of foam body 13 of securing unit 11 without compromising the firmness in the holding power of the securing unit 11.

Figure 8A:
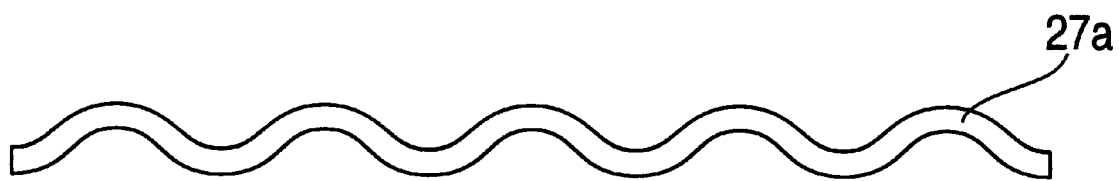
FIGS. 8A, B, C and D illustrate different types of single wave strip for embedding in the securing unit.
Figure 8B:
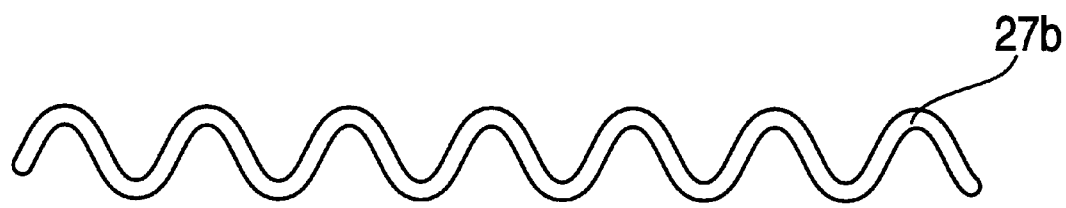
Figure 8C:
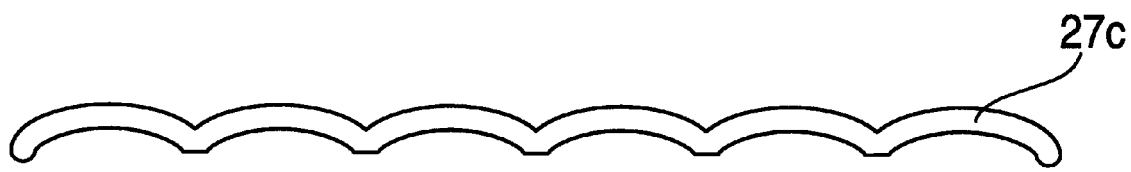
Figure 8D:
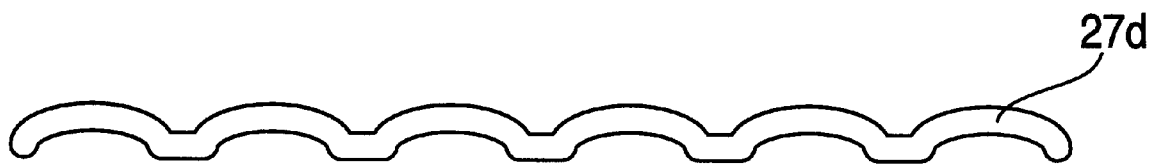

The plastic strips embedded in the body 13 of securing unit 11 may alternatively have different shapes and/or configurations. FIGS. 8A, B, C and D show four different types of single-wave strip 27a–d for embedding in the body 13 to reinforce the holding and stabilizing power of the securing unit 11. These four single-wave strips 27a–d vary in their wavelengths and styles and may be used for various applications.

Figure 9A:
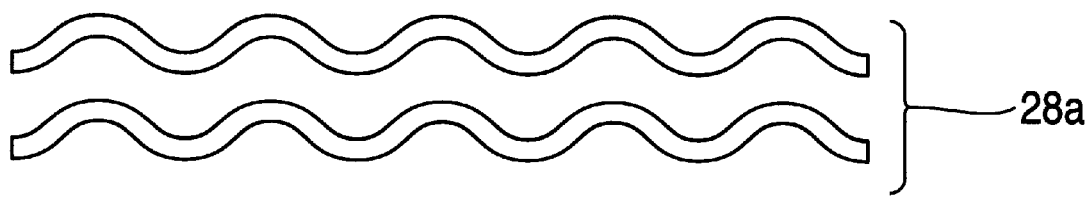
FIGS. 9A, B and C illustrate different types of double wave strip for embedding in the securing unit.
Figure 9B:
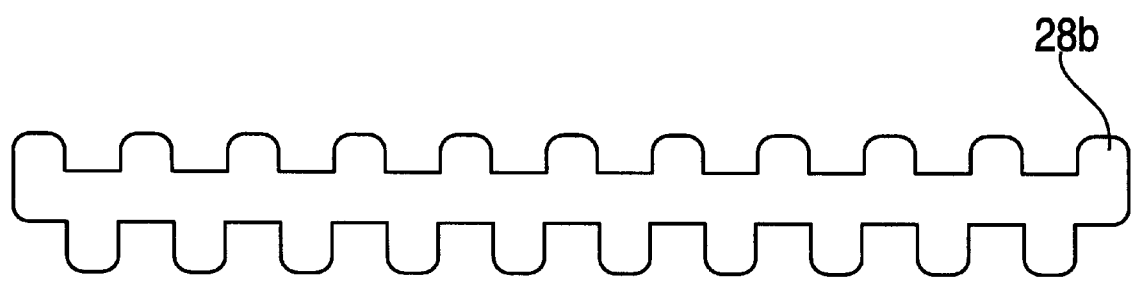
Figure 9C:
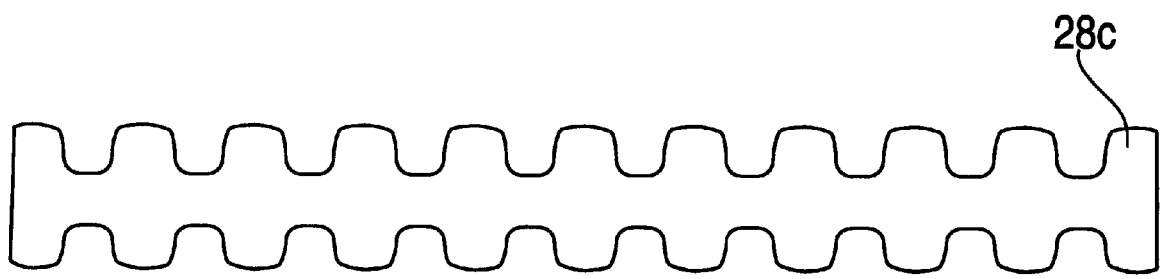

FIGS. 9A, B and C show three different types of double-wave strip 28a–c for embedding in the body 13 to further reinforce the holding and stabilizing power of the securing unit 11. These three double-wave strips 28a–c vary in their wavelength, width and relative positioning of the two waves, i.e. in phase (28a and 28b) and out of phase (28c) and may be used for various applications.

The single and double wave strips 27 and 28 may be embedded longitudinally in singular or in plurality in the body 13 in either a horizontal or vertical position relative to the top and bottom surfaces 14 and 15 of body 13 of the securing unit 11. FIG. 10 shows the present invention having two double wave strips 28a embedded longitudinally along body 13 of securing unit 11 in a horizontal position. Although two double wave strips 28a are shown to be embedded along opposite edges of the body 13, they may be embedded anywhere along body 13 and more or less double wave strips 28a–c may be used. The double wave strips 28a as shown in FIG. 10 reinforces and improves the holding and stabilizing power of the securing unit 11 without correspondingly increasing the size of the strips and provides added flexibility to mold and conform the securing unit 11 around the contour of a tube and/or catheter (not shown).

Figure 11:
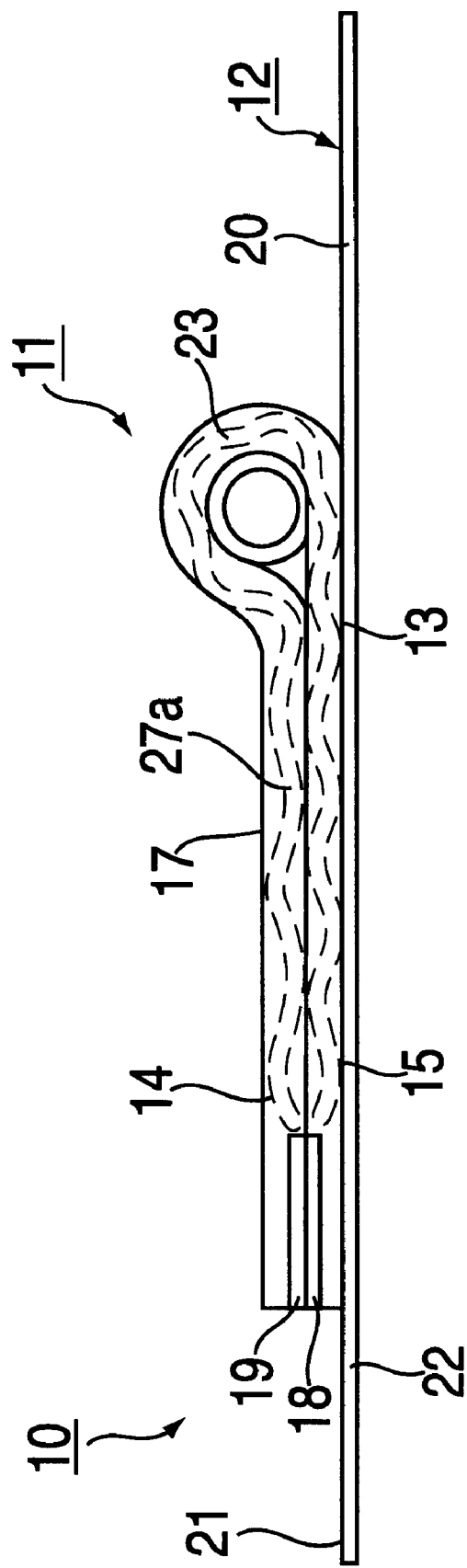
FIG. 11 is a front elevational view of the present invention with a single wave strip embedded vertically.

Similarly, as shown in FIG. 11, the single wave strip 27a embedded longitudinally along the body 13 of the securing unit 11 in a vertical position also reinforces and improves the holding and stabilizing power of the securing unit 11. When the securing unit 11 with the single wave strip 27a is embedded vertically, the single wave strip 27a maintains the form and reinforces the holding and stabilizing power of the securing unit 11 by stiffening the body 13 after being molded around the contour of tube 23. Furthermore, the indentation of each wave may be positioned or lengthened to correspond to the circumference of a tube and/or catheter such that minimal molding will be necessary to conform the securing unit 11 around the tube and/or catheter. One or more single wave strips 27a–d may be embedded in the body 13.

Figure 12:
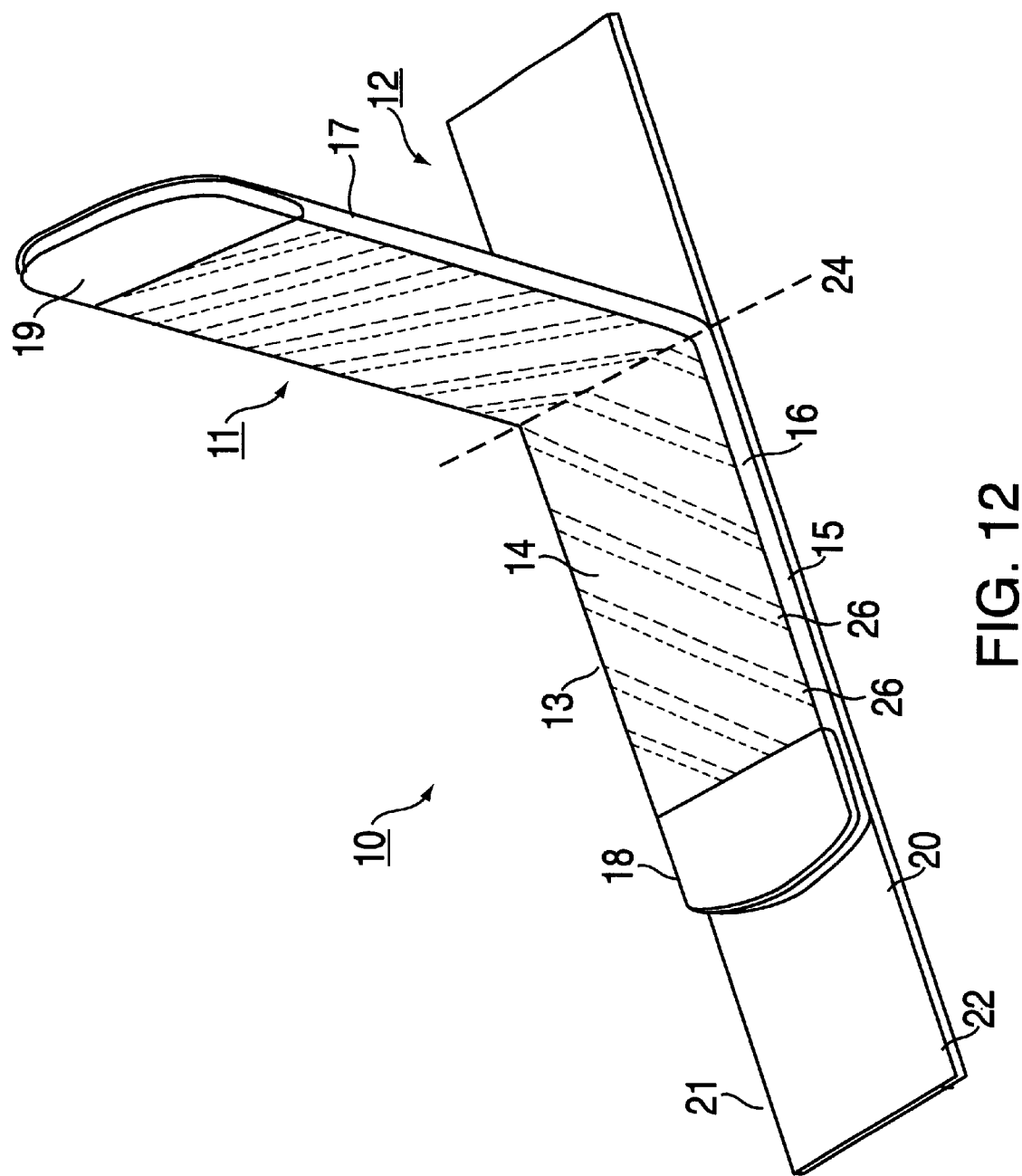
FIG. 12 is a perspective view of the present invention with a plurality of strips embedded in parallel, spaced-apart and at an angle with respect to the fold line.
Figure 13:
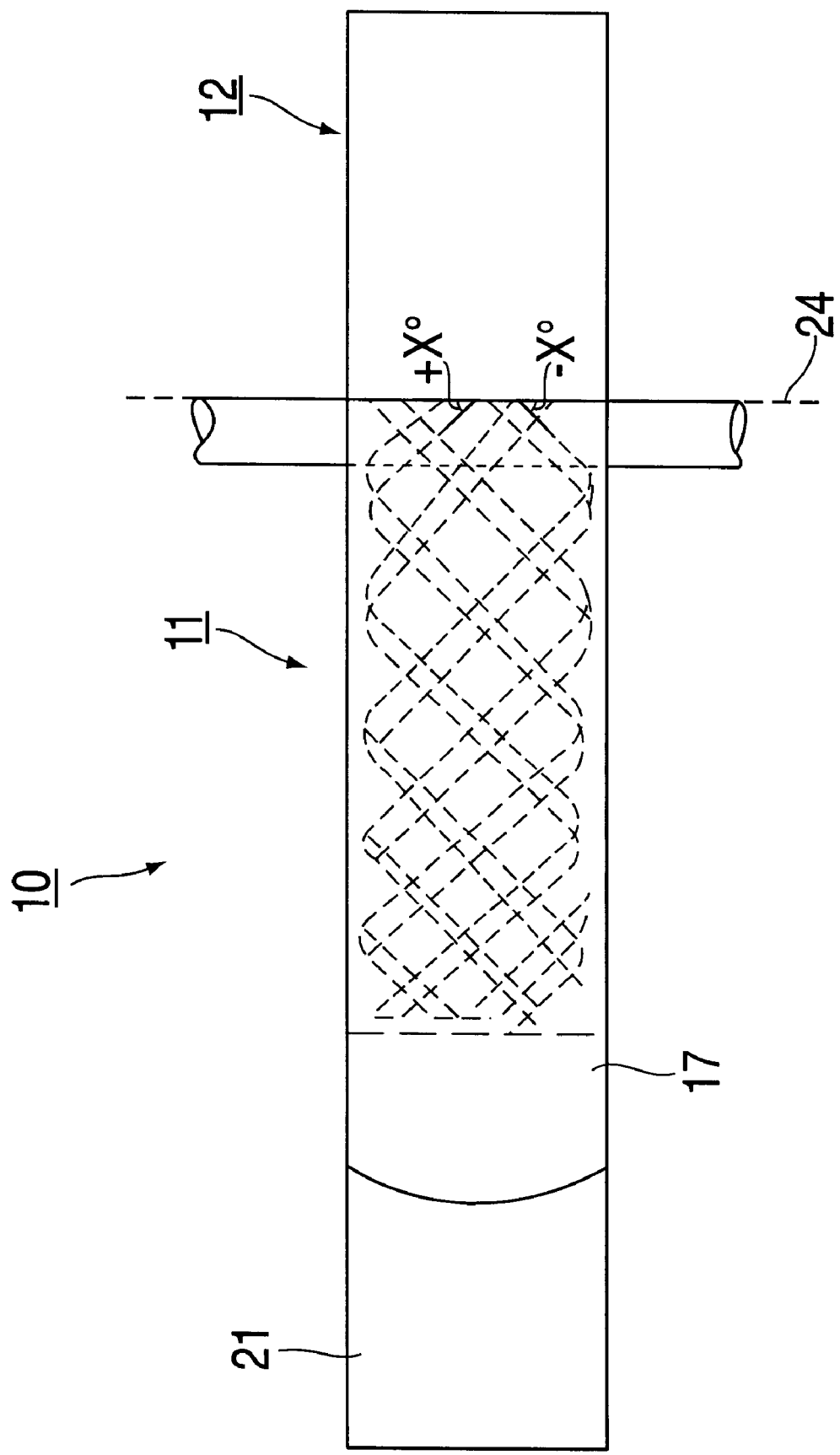
FIG. 13 is the top plan view of FIG. 12 illustrating a mesh pattern created by folding the second lateral portion over the first lateral portion of the body along the fold line.

In an alternative configuration, FIG. 12 shows a plurality of generally rectangular strips 26 embedded spaced-apart, in parallel, and at an angle relative to the fold line 24 of body 13 of the securing unit 11. By embedding a plurality of strips 26 at an angle, the plurality of strips 26 create a mesh or cross-hatch pattern when the first and second lateral portions 16 and 17 of body 13 overlap and overlay each other, as shown in FIG. 13. As shown in FIG. 13, the tube 23 positioned along the fold line 24 is held and stabilized in place by the plurality of strips 26 molded around the contour of tube 23. The plurality of strips 26 on the first lateral portion 16 molds around the tube 23 at a positive angle (+X°) relative to the fold line 24 and the plurality of strips 26 on the second lateral portion 17 molds around the tube 23 at a negative angle (−X°) to balance the forces exerted by the plurality of strips 26.

Figure 14:
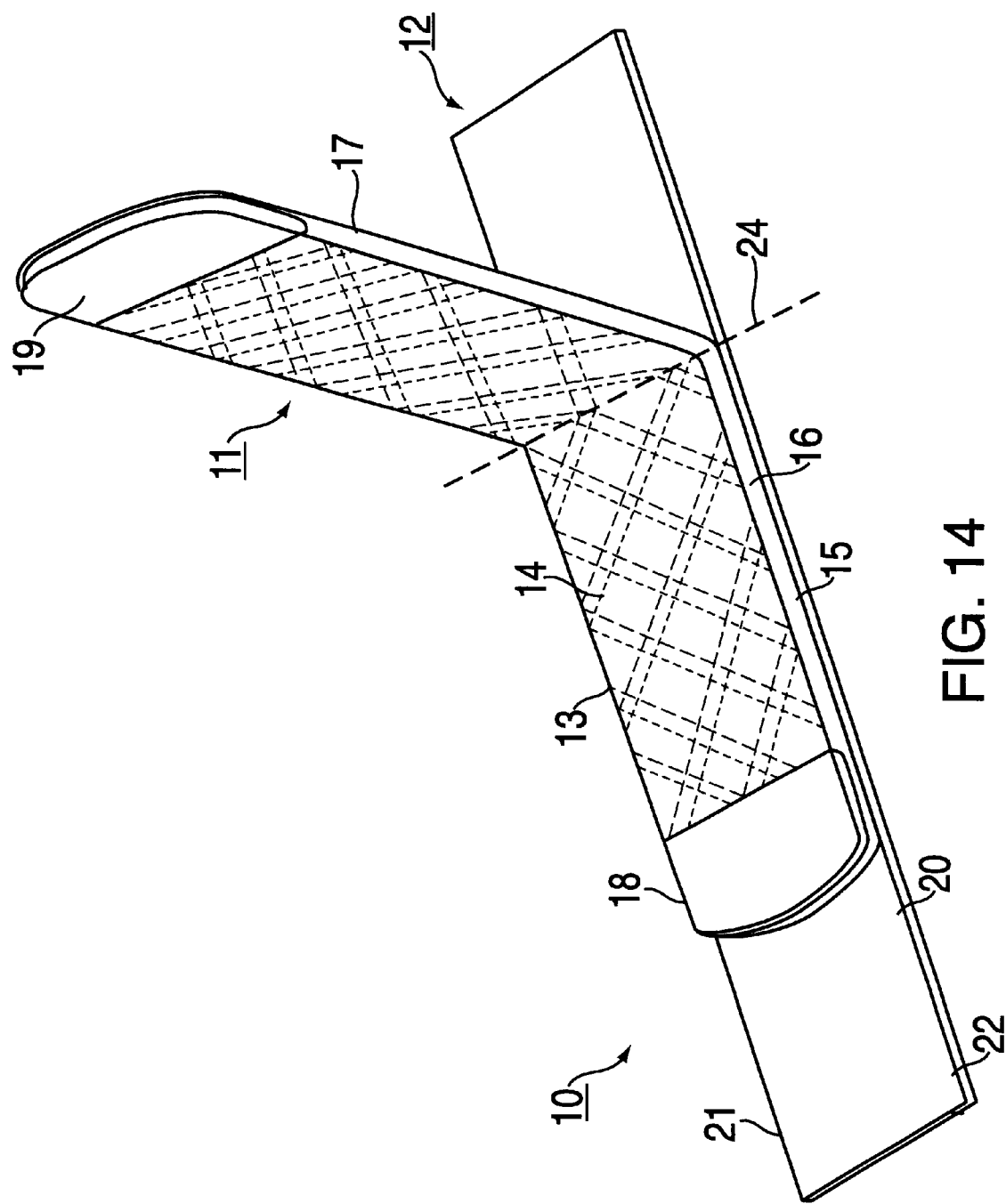
FIG. 14 is a perspective view of the present invention with a plurality of strips in a cross-hatch pattern embedded in the securing unit.

FIG. 14 shows a plurality of generally rectangular strips 26 embedded in a mesh or cross-hatch pattern, similar to the pattern achieved in FIG. 13 after the first and second lateral portions 16 and 17 are folded along fold line 24. The cross-hatch pattern exerts a balanced force against the tube and/or catheter positioned along the fold line 24 to reinforce and improve the holding and stabilizing power of the securing unit 11.

Figure 15:
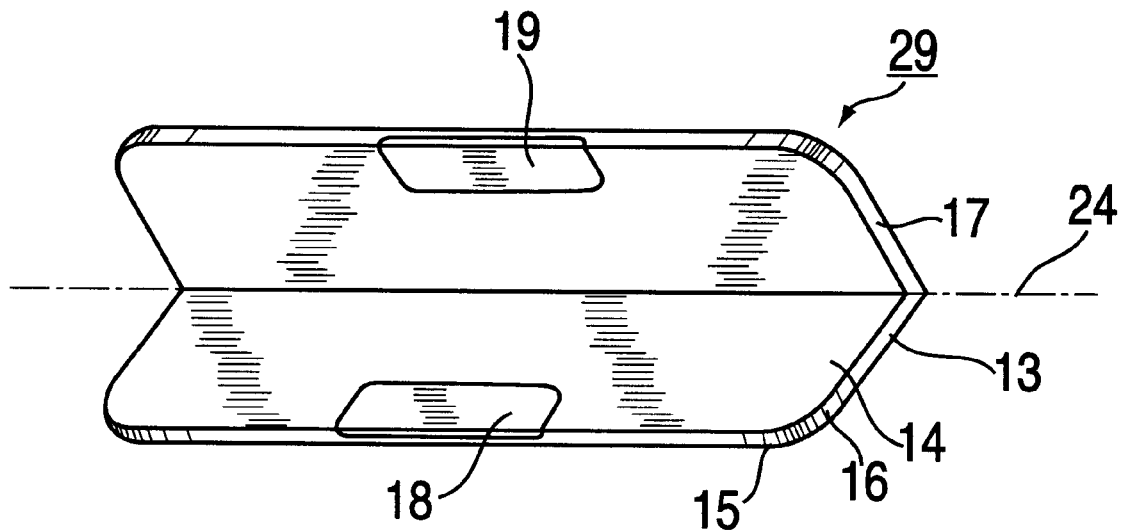
FIG. 15 is a perspective view of the modified securing unit for maintaining the shape and form of a cylindrical object.
Figure 16:
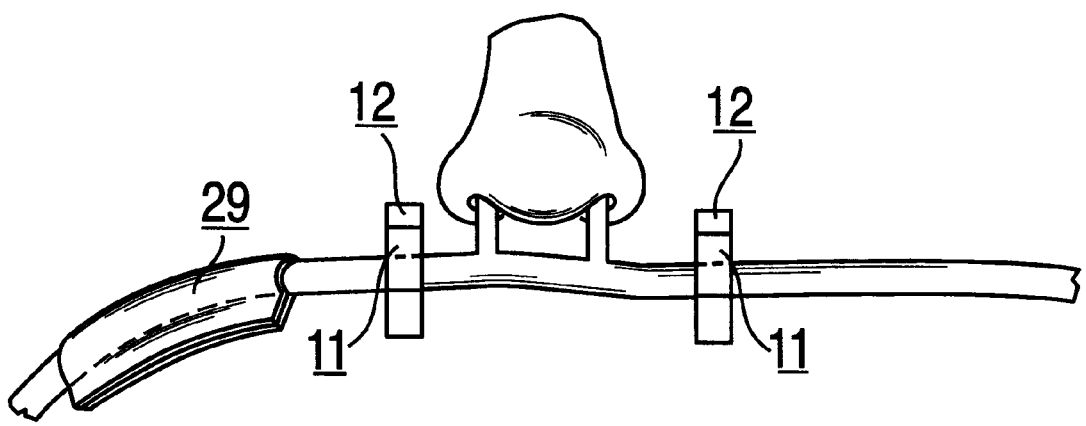
FIG. 16 illustrates the use of the modified securing unit of FIG. 15 alone to maintain the shape and form of a tube catheter and in conjunction with the anchoring unit to hold and stabilize the tube for a nasal gastric treatment.

The securing unit 11 with reinforced strips as shown in FIGS. 6, 10, 11, 12 and 14 may be used alone, without the anchoring unit 12, to maintain the shape and form of a tube and/or catheter. As shown in FIG. 15, the modified securing unit 29 is identical to the securing unit 11 but has a wider body 13. Modified securing unit 29 has a generally rectangular shaped body 13 having a top surface 14 and a bottom surface 15. Body 13 has first and second lateral portions 16 and 17, preferably of equal size, whereby the second portion 17 foldably overlays and overlaps the first portion 16. Top surface 14 of body 13 has resealable adhesive for securing a tube and/or catheter placed sandwiched between the first and second portions 16 and 17 along fold line 24, as shown in FIG. 16. At corresponding portions of each opposite end 18 and 19 of body 13, on the top surface 14, are corresponding hooks and loops, respectively, of a VELCRO™ interlocking mechanism. To maintain the shape and form of a tube and/or catheter placed in the modified securing unit 29, it is preferable that the body 13 of the securing unit 29 has one or more reinforcement strips 26, 27 or 28 embedded therein (not shown). The strips 26, 27 or 28 may take the forms shown in FIGS. 6, 10, 11, 12 or 14 to allow the securing unit 29 to mold or fold the tube and/or catheter placed therein to a certain shape or curvature, as shown in FIG. 16 for tubes used in a nasal gastric treatment. The modified securing unit 29 prevents a tube and/or catheter from being damaged or twisted, which affect the flow of treatment or drainage through the tube and/or catheter. Therefore, securing unit 11 or 29 serves the dual purpose of protecting and maintaining the shape of a tube and/or catheter when used alone and holding and stabilizing the tube and/or catheter when used in conjunction with the anchoring unit 12.

The modified securing unit 29 has other applications aside from the medical field. For example, it can be used to manage cables and/or wires by molding or conforming the cables and/or wires to certain shape and configuration that facilitates identification and/or separation when necessary.

Although certain features of the invention have been illustrated and described herein, other better modifications and changes will occur to those skilled in the art. It is, therefore, to be understood that the appended claims are intended to cover all such modification and changes that fall within the spirit of the invention.

What I claim is:

1. A device for securely retaining a tubular object comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and reinforcement means embedded non-longitudinally in said body for molding and conforming to said tubular object when said second portion foldably overlaps said first portion to retain said tubular object therebetween.

2. A device for securely retaining a tubular object comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and a plurality of plastic strips for molding and conforming to said tubular object are embedded in said body spaced-apart, in parallel and at an angle relative to said fold line such that a cross-hatch pattern is formed when said second portion foldably overlaps said first portion to retain said tubular object therebetween;

an anchoring unit for retaining said device at said fixed location; and means for attaching said securing unit onto said anchoring unit.

3. A device for securely retaining a tubular object comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and a plurality of plastic strips are embedded in said body to form a cross-hatch pattern for molding and conforming to said tubular object when said second portion foldably overlaps said first portion to retain said tubular object therebetween;

an anchoring unit for retaining said device at said fixed location; and means for attaching said securing unit onto said anchoring unit.

4. A device for securely retaining a tubular object comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and at least one plastic strip embedded in said body vertically relative to said top and bottom surfaces of said body for molding and conforming to said tubular object when said second portion foldably overlaps said first portion to retain said tubular object therebetween.

5. A device for securely retaining a tubular object comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and at least one generally rectangular shape plastic strip embedded in said body for molding and conforming to said tubular object when said second portion foldably overlaps said first portion to retain said tubular object therebetween.

6. A device for securely retaining a tubular object comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and at least one wave-like shape plastic strip embedded in said body for molding and conforming to said tubular object when said second portion foldably overlaps said first portion to retain said tubular object therebetween.

7. The device according to claim 6 wherein said wave-like shape plastic strip comprises a single wave-like shape.

8. The device according to claim 6 wherein said wave-like plastic strip comprises a double wave-like shape.

9. The device according to claim 8 wherein said double wave-like shape having a pair of waves in phase with each other.

10. The device according to claim 8 wherein said double wave-like shape having a pair of waves out of phase from each other.

11. A device for securely retaining a tubular object comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and a plurality of plastic strips for molding and conforming to said tubular object are embedded in said body spaced-apart, in parallel and at an angle relative to said fold line such that a cross-hatch pattern is formed when said second portion foldably overlaps said first portion to retain said tubular object therebetween.

12. A device for securely retaining a tubular object comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and a plurality of plastic strips are embedded in said body to form a cross-hatch pattern for molding and conforming to said tubular object when said second portion foldably overlaps said first portion to retain said tubular object therebetween.

13. A combination holding and stabilizing device for securely retaining a tubular object at a fixed location comprising:

a securing unit comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and at least one plastic strip embedded in said body vertically relative to said top and bottom surfaces of said body for molding and reinforcing to said tubular object when said second portion foldably overlaps said first portion to retain said tubular object therebetween;

an anchoring unit for retaining said device at said fixed location; and means for attaching said securing unit onto said anchoring unit.

14. A device for securely retaining a tubular object comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and at least one generally rectangular shape plastic strip embedded in said body for molding and conforming to said tubular object when said second portion foldably overlaps said first portion to retain said tubular object therebetween;

an anchoring unit for retaining said device at said fixed location; and means for attaching said securing unit onto said anchoring unit.

15. A device for securely retaining a tubular object comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position and at least one wave-like shape plastic strip embedded in said body for molding and conforming to said tubular object when said second portion foldably overlaps said first portion to retain said tubular object therebetween;

an anchoring unit for retaining said device at said fixed location; and means for attaching said securing unit onto said anchoring unit.

16. The device according to claim 15 wherein said wave-like plastic strip comprises a double wave-like shape.

17. The device according to claim 16 wherein said double wave-like shape having a pair of waves in phase with each other.

18. The device according to claim 16 wherein said double wave-like shape having a pair of waves out of phase from each other.

19. The device according to claim 15 wherein said wave-like shape plastic strip comprises a single wave-like shape.

* * * * *

UNITED STATES PATENT AND TRADEMARK OFFICE
CERTIFICATE OF CORRECTION

PATENT NO.    : 6,311,933 B1
DATED         : November 6, 2001
INVENTOR(S)   : Jovanka Starchevich It is certified that error appears in the above-identified patent and that said Letters Patent is hereby corrected as shown below:

<u>Column 7, line 52, Column 8, line 7, Column 10, line 14 and Column 10, line 35,</u>
Claims 2, 3, 14 & 15:
Replace the first line of each claim, the words "A device for securely retaining a tubular object" with -- A combination holding and stabilizing device for securely retaining a tubular object at a fixed location comprising: a securing unit --

Signed and Sealed this

Twenty-fourth Day of December, 2002

JAMES E. ROGAN
*Director of the United States Patent and Trademark Office*